United States Patent [19]
Eveland

[11] 3,965,576
[45] June 29, 1976

[54] DENTAL APPARATUS AND METHOD

[76] Inventor: Melborne D. Eveland, 1006 Buena Vista Road, Forked River, N.J. 08731

[22] Filed: May 15, 1974

[21] Appl. No.: 470,197

[52] U.S. Cl. .................................................. 32/32
[51] Int. Cl.². ........................................ A61C 11/00
[58] Field of Search .......................................... 32/32

[56] References Cited
UNITED STATES PATENTS

| | | | |
|---|---|---|---|
| 3,043,009 | 7/1962 | Whitman | 32/32 |
| 3,750,289 | 8/1973 | Guichet | 32/32 |
| 3,808,689 | 5/1974 | Spinella | 32/32 |
| 3,815,242 | 6/1974 | Martfay et al. | 32/32 |

*Primary Examiner*—Robert Peshock
*Attorney, Agent, or Firm*—Robert K. Youtie

[57] ABSTRACT

A dental method and apparatus wherein detachably assembled dental models are provided with generally parallel opposite faces by an improved surfacing device of the present invention, the parallel faces having secured thereto respective attachment members or shims which are properly located by use of an improved jig, and wherein the dental models may be removably mounted in proper location in a novel articulator by the attachment members, and be removably replaceable in proper location within the articulator.

9 Claims, 15 Drawing Figures

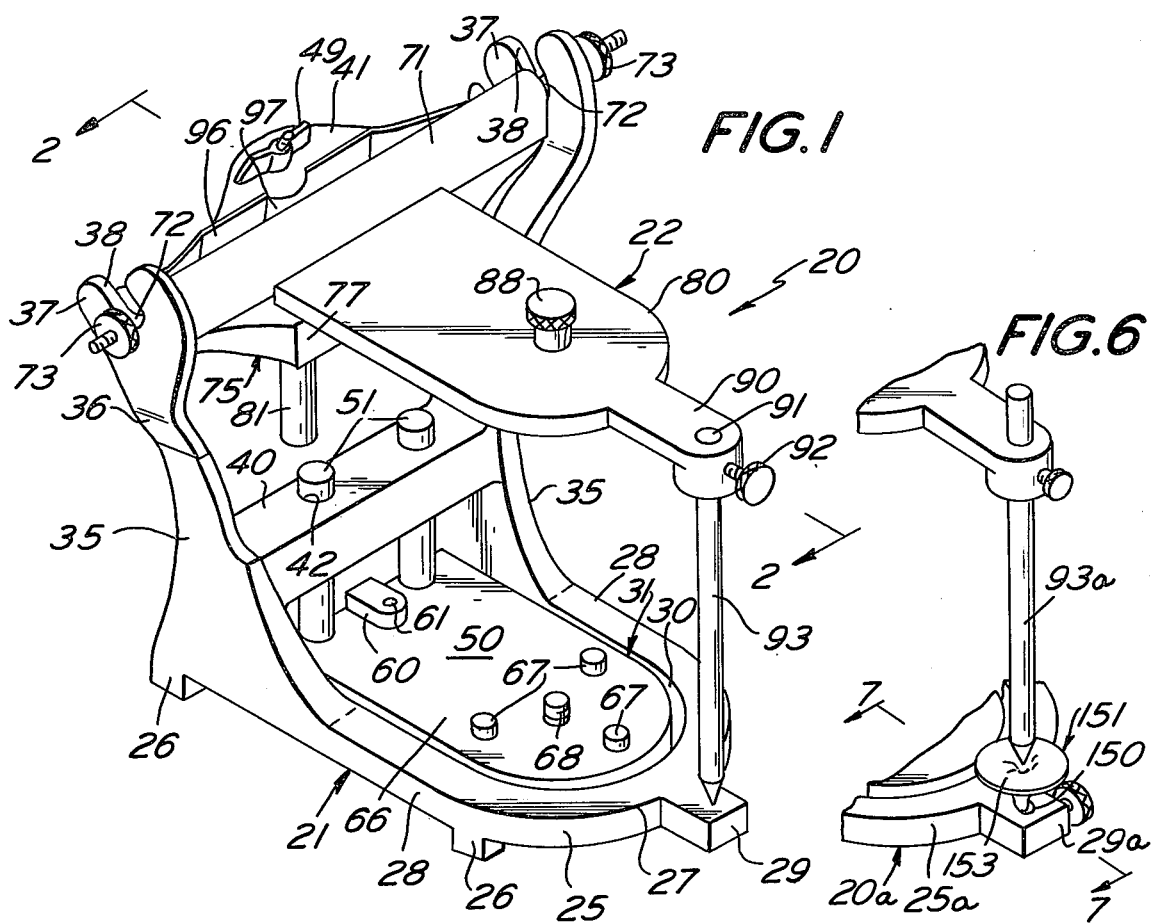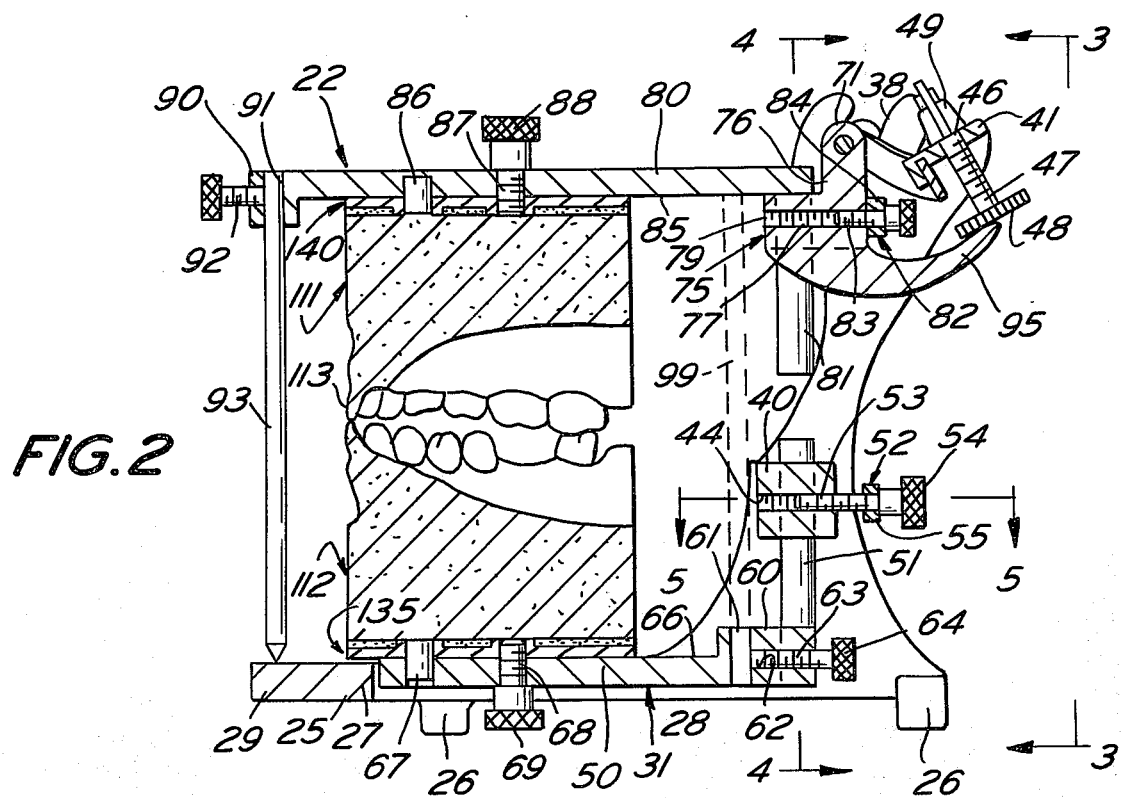

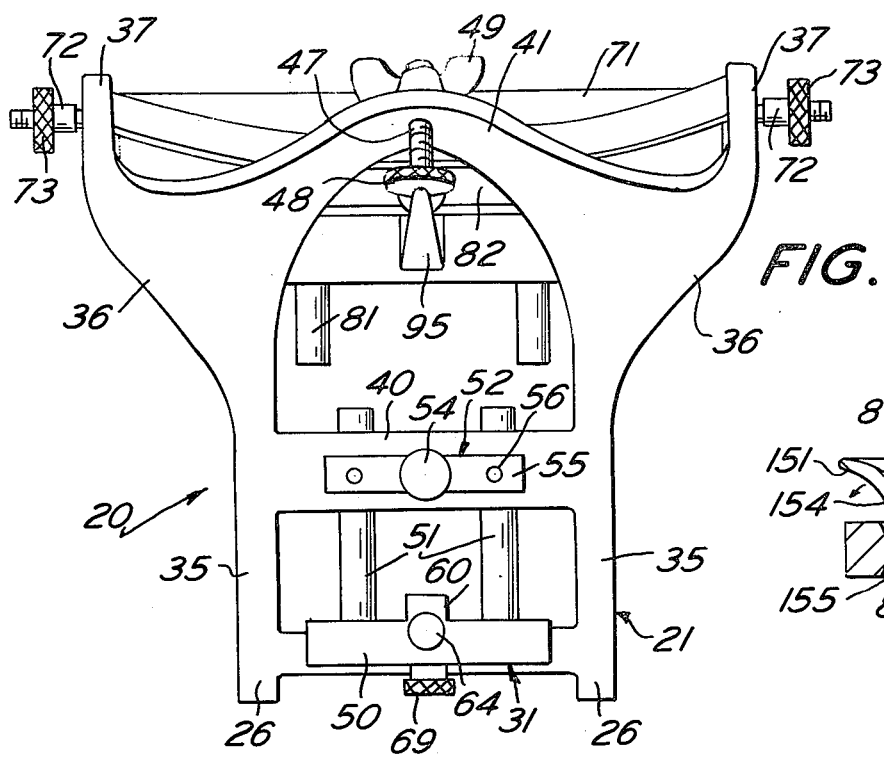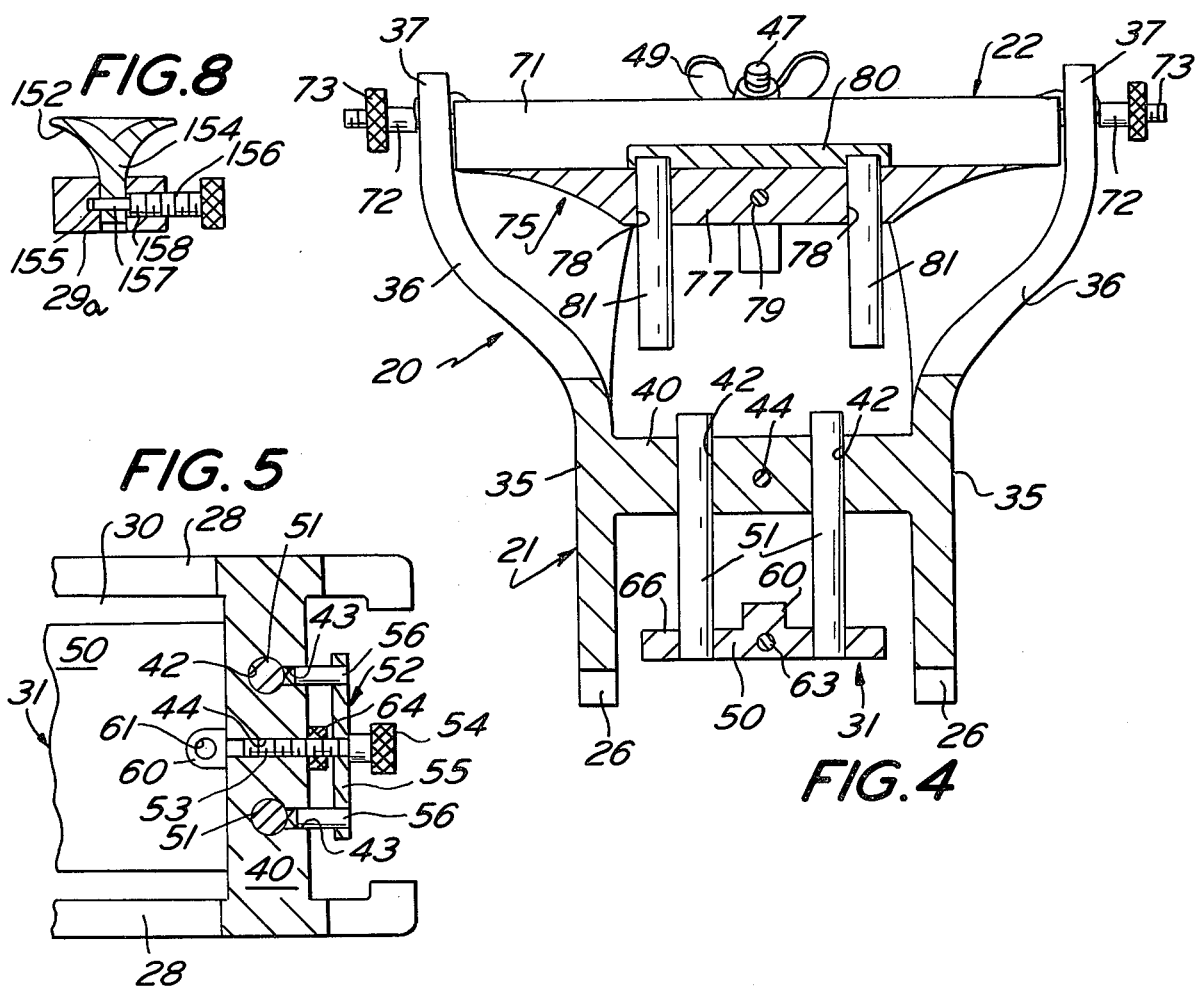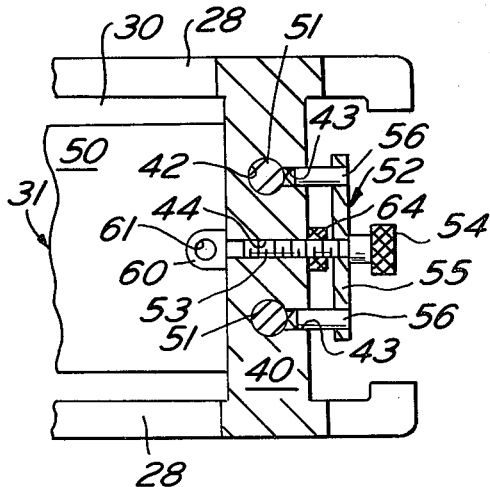

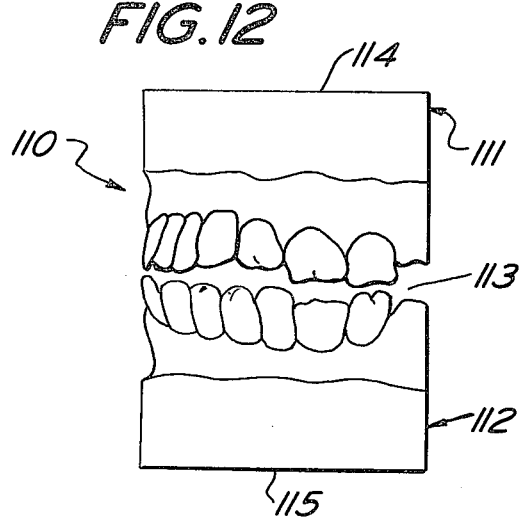
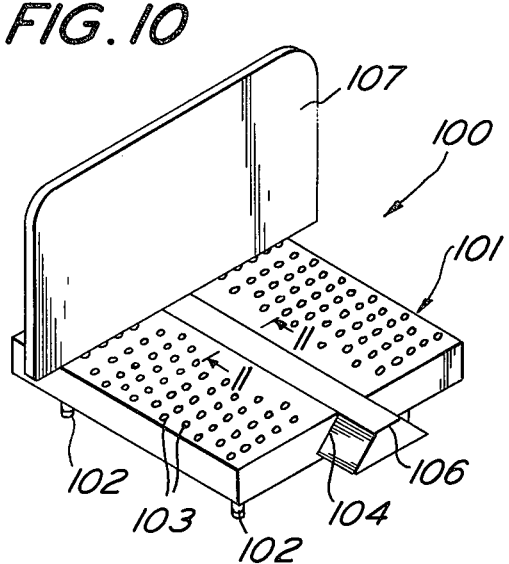
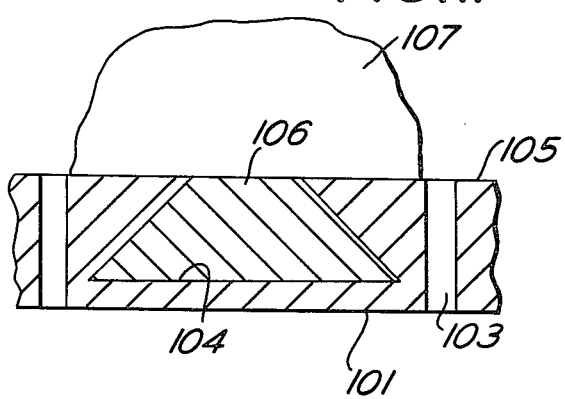
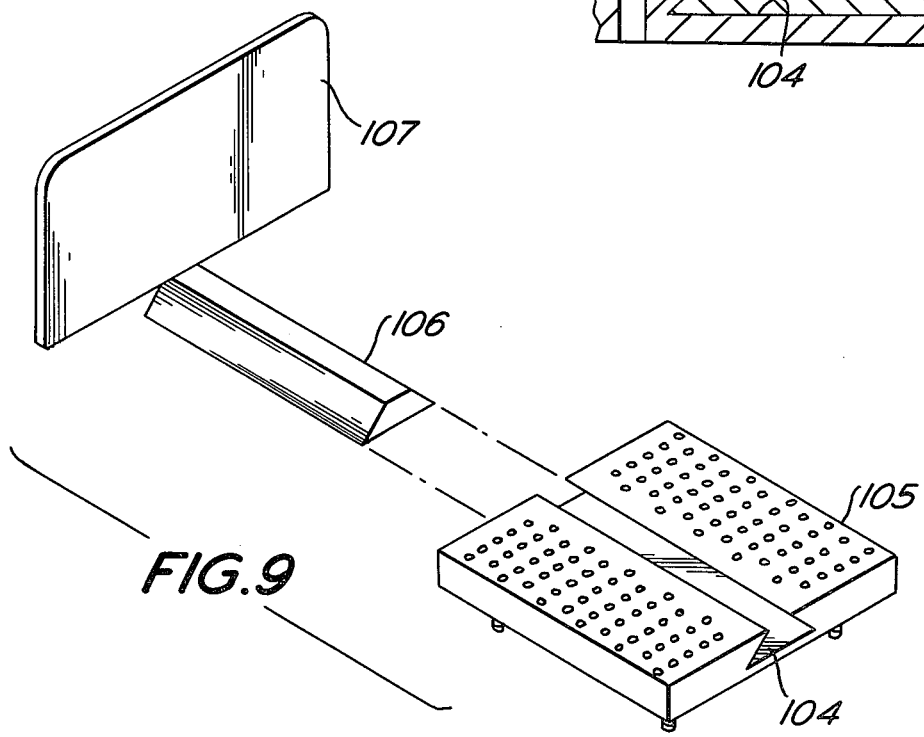

DENTAL APPARATUS AND METHOD

BACKGROUND OF THE INVENTION

As is well known to dental technicians, and those versed in the field, the fabrication of dentures, both partial and complete, is largely an art, requiring highly skilled personnel having considerable experience, the present methods involving considerable judgement, many tedious operations and being very time-consuming.

SUMMARY OF THE INVENTION

It is an important object of the present invention to provide improvements in a dental method and apparatus whereby dental technicians may more easily, quickly and accurately fabricate a wide variety of dentures, to effect substantial savings in costs, time of the dentist and technician, and with resultant improvements in dentures.

It is a further object of the present invention to provide a dental method and apparatus of the type described wherein dental models may be removably replaceable with respect to different articulators of the present invention with ease and rapidity, and without loss of precise location; enabling dental models to be sent to dentists without articulators for reduction in shipping costs and required number of articulators; and wherein less plaster is required and the articulators are not involved in any grinding or hammering for greatly increased articulator life.

It is still a further object of the present invention to provide a method and apparatus having the advantageous characteristics mentioned in the preceding paragraph, which may be employed with face-bow technique, being lockable in centric position and accurately shifted as desired.

It is a more particular object of the present invention to provide apparatus of the present invention auxiliary to the articulator for conveniently servicing opposite faces of a dental model assembly, and quickly and easily mounting attachment members to the dental models for releasable attachment to the articulator.

Other objects of the present invention will become apparent upon reading the following specification and referring to the accompanying drawings, which form a material part of this disclosure.

The invention accordingly consists in the features of construction, combinations and arrangements of parts and method steps, which will be exemplified in the following description, and of which the scope will be indicated by the appended claims.

BRIEF DESCRIPTION OF THE DRAWINGS

FIG. 1 is a top, front perspective view showing an articulator constructed in accordance with the present invention.

FIG. 2 is a sectional elevational view taken generally along the line 2—2 of FIG. 1, and illustrating dental models mounted in the articulator.

FIG. 3 is a rear elevational view of the articulator, as taken generally along the line 3—3 of FIG. 2.

FIG. 4 is a sectional elevational view taken generally along the line 4—4 of FIG. 2.

FIG. 5 is a partial horizontal sectional view taken generally along the line 5—5 of FIG. 2.

FIG. 6 is a partial front perspective view similar to FIG. 1, but showing a slightly modified embodiment.

FIG. 7 is partial sectional elevational view taken generally along the line 7—7 of FIG. 6. FIG. 8 is a sectional elevational view taken generally along the line 8—8 of FIG. 7.

FIG. 9 is an exploded perspective view showing a handling apparatus or work tray for use in surfacing dental models.

FIG. 10 is a perspective view showing the work apparatus or tray of FIG. 9, but assembled.

FIG. 11 is a partial sectional elevational view taken substantially along the line 11—11 in FIG. 10.

FIG. 12 is a side elevational view showing a dental model assembly in centric position.

DESCRIPTION OF THE PREFERRED EMBODIMENTS

Figure 13:
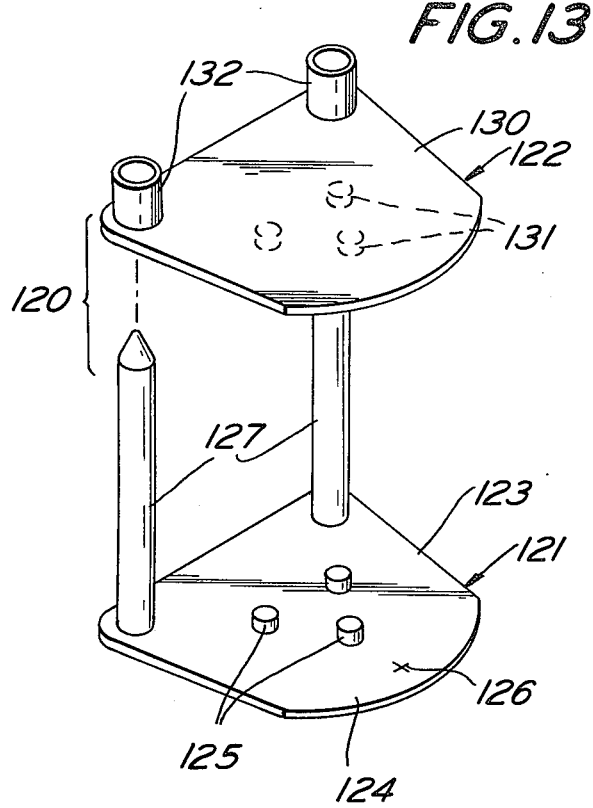
FIG. 13 is a top perspective view showing a work positioning apparatus of jig of the present invention.

Referring now more particularly to the drawings, and specifically to FIGS. 1–5 thereof, an articulator of the present invention is there generally designated 20 and includes a base or stand 21 adapted to rest on a support, and an upper member 22 carried for rotation about an elevated generally horizontal axis. The articulator base 21 may include a generally horizontal open frame 25 normally disposed substantially horizontally and having at spaced locations thereabout depending feet 26 for supporting engagement with a nether surface. The base frame 25 may be generally U-shaped, as illustrated, including a forward bight portion 27 and side legs 28 extending from opposite ends of the bight portion. Extending forwardly from a medial region of the bight portion 27 may be an arm, projection or lug 29. The space bounded within the generally U-shaped frame 25 may be open, as at 30, and located in spaced relation within the opening 30 may be a generally horizontally disposed plate-like lower member 31.

Upstanding from the rear end of each leg 28 may be an upstanding member or pedestal 35. That is, a pair of laterally spaced pedestals 35 upstand from respective rear regions of frame legs 28, and are formed with upwardly and laterally outwardly diverging regions terminating at their upper ends in portions 37 defining journal bearings. That is, the upper end portions 37 are each provided with a rearwardly inclined slot 38, opening upwardly and in lateral alignment with each other.

A lateral or bridging member 40 extends generally horizontally between vertically intermediate regions of the pedestals 35, and an upper bridging member or arch 41 extends laterally between upper laterally outwardly diverging regions 36 of the pedestals 35, adjacent to and below the bearing portions 37.

The lower lateral member 40 may be provided with a pair of laterally spaced, generally vertical through openings or guide holes 42, best seen in FIGS. 4 and 5. Extending forwardly and rearwardly, inwardly from the rear side of lateral frame member 40, intersecting with respective guide holes 42 are holes or openings 43, while an additional forwardly and rearwardly extending hole 44 passes generally horizontally through the lateral member 40 spaced intermediate the hole 43 and having internal screw threads, all for a purpose appearing presently.

The upper lateral bridging member 41 is provided medially with an internally threaded through hole 46 extending generally at an oblique angle forwardly and upwardly. The hole 46 may receive, in threaded engagement, a threaded shank 47 having an enlarged head 48 on its lower end spaced beneath the medial region of bridge 41. Above the bridge 41, threadedly engaged on the upper end of shank 47, may be a nut 49. Thus, the head 48 may be selectively vertically positionable as by rotation of shank 47 in hole 46 and adapted to be releasably locked in any selected position, as by jamming of nut 49 against the bridge 41.

The lower member 31 may include generally flat plate 50 disposed horizontally and configured for conformably received spaced relation within the opening 30 of frame 25. The plate 50 may be provided at its rearward region with a pair of generally parallel, laterally spaced upstanding pins or posts 51, which extend upwardly into and slidably through the holes 42 of lateral member 40. Thus, the plate 50 of lower member 31 is selectively locatable in its horizontal disposition at a desired elevation, as by sliding movement of the mounting pins 51 through holes 42. The mounting pins 51 may be fixed to the plate 50 by any suitable means.

In order to releasably hold the lower plate 50 at a selected elevation, there is provided a holding device 52 including a screw 53 threadedly engaged in hole 44 and having an enlarged knurled head 54 rearward of the lateral member 40. Rotatably carried by the screw 53 is a cross-piece 55 which is provided at its opposite ends with a pair of holding members or pins 56 respectively slidably entering into holes 43 for releasable holding engagement with the mounting pins 51. That is, the screw 44 is threadedly engageable forwardly and rearwardly to shift the holding pins 56 forwardly and rearwardly into and out of holding engagement with the mounting pin 51 to effectively lock the latter at a selected position of their sliding movement according to the desired elevation of plate 50.

The plate 50 may further be provided at its rearward region with a boss 60, and there may be formed extending generally vertically through the boss and plate 50 a passageway or hole 61 located in a plane just forward of the lateral member 40. A generally forwardly and rearwardly extending internally threaded hole 62 enters into the rear side or edge of plate 50 and boss 60, and opens into or intersects with the vertical hole 61, while a threaded member or set screw 63 may extend in threaded engagement into the hole 62, projecting rearwardly therefrom and provided on its projecting end with an enlarged actuating element or head 64.

The upper surface 56 of plate 50 is generally flat and is provided in its forward region with a plurality of upstanding lugs or bosses, say being three in number, and arranged in triangular relation, as at 67. A rotary threaded member 68 or other suitable fastener may upstand through the upper surface 66 of plate 50, being provided on its lower end beneath the plate with an actuating member or head 69.

The upper member 22 includes a generally horizontal, laterally extending rotary member or shaft 71 extending between the upper end regions 37 of the pair of pedestals 35. In addition, the shaft 71 is provided at opposite ends with a pair of oppositely outwardly projecting, axial extensions or bearing portions 72 respectively rotatably received and journaled in slots 38 of journal bearings 37. Longitudinal sliding of shaft 71 between journal bearings 37 may be effectively prevented by abutting engagement with the latter. The extensions 72 may be threaded on their outer or terminal portions and there provided with nuts, as at 73.

A generally angulate formation 75 is provided on the shaft 71, including a generally depending portion 76, and a ledge portion 77 projecting forwardly from a lower region of the depending portion. That is, the ledge 77 extends laterally and forwardly approximately over the lower lateral member 40. The laterally extending ledge 77 is provided with a pair of laterally spaced, vertically extending through openings or holes 78, and a forwardly and rearwardly extending internally threaded hole 79 is provided in the ledge 77 spaced between the holes 78. Additionally, a pair of forwardly and rearwardly extending, laterally spaced generally horizontal holes are provided in ledge 77, similar to the holes 43 of lateral member 40, but intersecting with holes 78, and not shown in the drawing.

The upper member 22 further includes a generally flat plate 80 extending from said shaft 71, approximately radially thereof, generally horizontally forwardly to spacedly overlie the lower plate 50. The upper plate 80 may have fixedly depending from the rearward region thereof a pair of mounting pins 81 located in laterally spaced relation and extending slidably through respective holes 78. Thus, the upper plate 80 of upper member 22 is mounted with its rearward region in parallel facing relation with the ledge 77, and is selectively adjustable toward and away from the latter by sliding movement of pins 81 in hole 78. Releasable holding means 82, similar to the releasable holding means 52, may be carried by the angulate bracket formation 75, see FIG. 2, including a headed screw 83 threadedly engaged in hole 79 and a cross piece 84 carried by the screw 83 and, in turn, carrying spaced holding pins (not shown) for releasable holding engagement with respective guide pins 81, in the same manner as holding pins 56. Thus, plate 80 of upper member 22 is adjustable along the axes of mounting pins 81, generally transverse of the axis of shaft 71, and carried for swinging rotation about the latter.

The generally flat undersurface 85 of upper plate 80 may be provided with a plurality of fixed, depending locators or lugs 86, say a triangular arrangement as the lugs 67 of the lower plate 50. Centrally of the locator lugs 86, the plate 80 may be provided with a through fastener 87, such as a rotatable screw having an enlarged head 88 above the upper plate, and having its threaded end projecting below the upper plate.

From the forward end of the plate 80, generally over the extension or ear 29, there is provided a forward extension or ear 90 having its distal region of increased vertical dimension or depth and provided therethrough with a vertical hole 91. A threaded holding member or set screw 92 is engaged into the ear 90 for intersection with the hole 91 to releasably hold a depending pin 93. That is, the pin 93 may depend into bearing engagement with the ear 29 for properly spacing and rigidifying the relationship between the upper member 22 and lower member 21, as will appear more fully hereinafter.

A stop member 95 may extend from the angulate formation 75, say from the underside of ledge portion 77, rearwardly and arcuately upwardly, best seen in FIG. 2. It will there be observed that the distal end of the stop member 95 is engageable with the adjustable head 48 for limiting downward swinging movement of the upper member 22.

The entire upper member 22 may be removable from the lower member 21 and pedestals 25, as by upwardly and rearwardly withdrawing the shaft bearing portions 72 from the journal slots 38. However, the shaft bearing portions 72 are releasably retained in the journal slots 38 by a leaf spring 96 medially anchored, as by a retainer 97 to the front side of arch 41, and having its opposite distal ends freely resiliently retaining shaft portions 72 in journal bearings 38. The shaft 71 may be removed by exerting sufficient force to resiliently deflect the spring 96 for removal of the shaft portions from their receiving slots.

Referring now to FIGS. 9–12, and particularly to FIGS. 9 and 10, a work handling device is there generally designated 100 and is adapted for use in conjunction with a conventional dental trimmer or grinder. The handling device includes a generally horizontal tray 101 for mounting on a trimmer, as by feet 102, or other suitable means. The tray 101 may be apertured or perforated, as at 103 for freely passing water or liquid, and is advantageously formed with a guideway or slot, as at 104, say of dovetail configuration and opening through the upper tray surface 105. A key or slide 106 is conformably received in the slot 104 for sliding movement therein, and is provided with an upstanding pusher member or guide plate 107 disposed generally normal to the tray surface 105. By this means, a workpiece may be pushed by the guide plate 107, while resting on the tray surface 105, against a grinder or trimmer to finish one surface of the work generally parallel to the guide plate.

In FIG. 12 is shown an assembled dental model 110 including an upper dental model 111 and a lower dental model 112, which are assembled together in proper centric relation and detachably secured together by suitable means, such as with wax 113. In the assembled condition one surface of the assembly, say the upper surface 114 is finished generally parallel to the occlusive plane, say on a grinder or trimmer, and the other, opposite surface 115 may then be readily finished parallel to the surface 114 by use of the handling device 100. That is, the previously finished surface 114 may be held flat against the guide plate 107 and moved together with the latter toward the trimming station for finishing surface 115 parallel to the guide plate and first finished surface.

The various additional surfaces of the models 111 and 112 may be similarly finished on a trimmer and using the work handling device 111, with the models in assembled condition.

Figure 14:
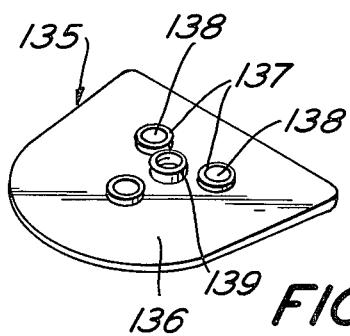
FIG. 14 is a perspective view showing a shim or attachment member of the present invention.
Figure 15:
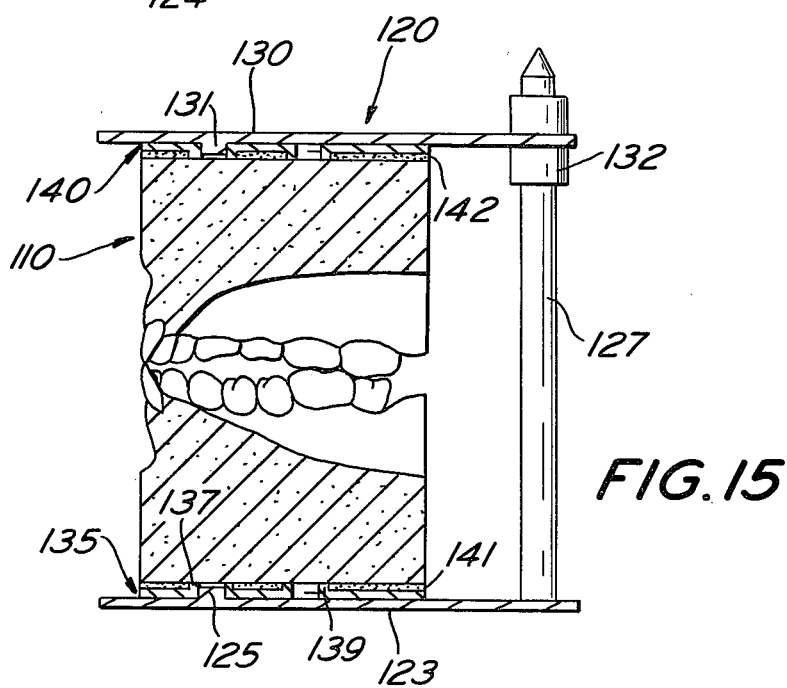
FIG. 15 is a sectional elevational view showing an assembled jig, together with a dental model assembly and attachment members.

Referring now to FIGS. 13—15, a jig is shown in FIGS. 13 and 15 and there generally designated 120. The jig includes lower and upper members, respectively generally designated 121 and 122. The lower member includes a generally horizontal lower plate or base 123 provided on its upper surface 124 with a plurality of upstanding locating formations or lugs 125, say corresponding in size and configuration to the locating formations or lugs 67 and 86 of articulator plates 50 and 80. Also, a registration or locating mark 126 may be provided on the upper surface of lower jig plate 123.

Upstanding from rearward regions of the lower jig plate 123 may be a pair of generally parallel, rigid pins or posts 127.

The upper jig member 122 includes a generally flat upper jig plate 130, which may be substantially congruent to the lower jig plate 123, being provided on its underside with a plurality of locating formations or depending lugs 131 corresponding in size and arrangement to the lugs 125. Rearward regions of the upper jig plate 130 may be provided with open ended tubes or bushings defining through passageways for slidably receiving respective posts or pins 127.

In addition, see FIG. 14, there are provided a pair of shim plates or attachment members 135, each consisting of a relatively stiff, substantially flat plate 136 preferably fabricated of material adapted to be easily worked, as for removal in the dental model trimming operation. Various plastics are believed entirely satisfactory.

The shim plate or attachment member 135 is formed on one surface with a plurality of hollow, generally cylindrical upstanding lug receiving formations 137, each bounding and defining therewithin a through opening or hole 138. The size, configuration and arrangement of the cylindrical formations or bushings 137 is such as to conformably receive the locating lugs 125 and 131 of the jig plates, and also the locating lugs 67 and 86 of the articulator plates. Additionally, the shim plate or attachment member 135 may be provided with an internally threaded hollow receiver or bushing 139 located and configured to receive an articulator fastener 69, 87.

In use, a pair of attachment members or shim plates, as at 135 and 140 are located on respective lower and upper jig plates 123 and 130, and the dental model assembly 110 is interposed therebetween with the dental models adhesively or otherwise suitably secured, as by cement 141 and 142 to respective shim plates or attachment members.

The model assembly 110, together with the attachment members or shim plates 135 and 140 secured to the model assembly, may now be removed from the jig 120 and placed in the articulator 20, with attachment members 135 and 140 properly located by receiving respective locating pins 62 and 86. Also, the fasteners 68 and 87 may be threadedly engaged in respective attachment members to assure retention thereof in position on the articulator plates 50 and 80.

A bight pin (not shown) may be inserted upwardly through hole 61 to abut the undersurface of plate 80. The bight pin may be secured in position by set screw 63 and severed flush with the underside of lower plate 50. The wax 113, retaining the dental models 111 and 112 assembled, may be removed, and the models will remain in centric position. Further, centric position may be repeated, as desired, after removal of the models 111 and 112 from the articulator, by merely replacing the models by their attachment members 140 and 135, and reinserting the hereinbefore described bight pin 99 flush with the lower end of hole 61.

Considering now the modifications shown in FIGS. 6, 7 and 8, an articulator 20a includes a lower frame 25a generally similar to the frame 25 of the first described embodiment, and provided with a forward extension or ear 29a. However, the ear 29a includes a vertically extending through slot 150 directly beneath the lower end of pin 93a.

An incisal cup is generally designated 151 and includes a cup proper 152 having an internal upper surface 153 of internal cusp-shaped configuration facing generally upwardly. Depending from the underside of the cup proper 152 is a stem or shank 154 having an eye 155 located in the slot 150. A threaded and headed pin 156 may extend threadedly into the ear 29a, including a cylindrical portion 157 entering into the eye 155 of shank 154 to rotatably support the cup 151. However, upon rotation of the fastener 156 inward, the shank may be clamped in any desired position of rotation, as by bearing engagement with the shank of annular shoulder 158 on the fastener 156.

It will be appreciated by those skilled in the art that, when the articulator is moved to its protrusive mode, the upper member rearwardly, the incisal guide cup may be tilted rearward to reduce the opening, and forwardly to increase the opening.

From the foregoing it is seen that the present invention provides a method and apparatus which greatly facilitate the fabrication of dentures, reducing the time and costs to both the dentists and the dental technician, while enhancing accuracy, and otherwise fully accomplish their intended objects.

Although the present invention has been described in some detail by way of illustration and example for purposes of clarity of understanding, it is understood that certain changes and modifications may be made within the spirit of the invention.

What is claimed is:

1. In a dental method, the steps which comprise: detachably assembling upper and lower dental models in centric relation, surfacing opposite faces of the assembly generally parallel to each other and to the occlusal plane, positioning said assembly in a locating jig having a predetermined spacial relation with respect to an articulator, fixedly adhering attachment members to said opposite faces in said locating jig, removing said assembly and fixed attachment members from the jig, disassembling said models from said assembly, detachably mounting said models by said attachment members on the respective upper and lower members of an articulator for centric location of the models in said articulator, and providing an internal cusp-like guide surface fixed relative to said lower articulator member, and a follower depending from said upper articulator member into following engagement with said guide surface, for movement of said upper member relative to said lower member with said follower on said guide member to simulate excursive movement.

2. A dental articulator comprising a base adapted to rest on a supporting surface, a lower member in upwardly facing relation on said base for detachably carrying a lower dental model, upstanding pedestal means on said base, bearing means at an upper region of said pedestal means, journal means rotatably supported by said bearing means, an upper member extending from said journal means in downwardly facing relation over said lower member for detachably carrying an upper dental model and rotatable with said journal means for moving said dental models toward and away from each other, lower adjustment means mounting said lower member for selective vertical adjustment relative to said base, upper adjustment means mounting said upper member for selective adjustment transverse of said journal means toward and away from said lower member, said upper and lower members being adjustable to position the occlusal plane of said models, a vertical bight pin receiver in said lower member adjacent to said pedestal means, a vertical bight pin slidable in said receiver to locate its upper end for abutting engagement with said upper member, and releasable locking means for locking said pin at a selected position in said receiver.

3. A dental articulator according to claim 2, in combination with releasable fastener means on said upper and lower members, and attachment members for fixed securement to upper and lower dental models, said attachment members including complementary fastener means for detachable fastening of said attachment members to the respective upper and lower members.

4. A dental articulator according to claim 3, in combination with locating elements on said attachment members, a model positioning jig, complementary locating elements on said jig for interfitting relation with said attachment member locating elements, and additional conplementary locating elements on said upper and lower members for interfitting relation with said attachment member locating element, for similar location of said attachment members relative to said jig and upper and lower members.

5. An articulator according to claim 2, in combination with a strut depending from said upper member into end abutting engagement with said base for limiting free rotation and deflection of said upper member toward said lower member.

6. A dental articulator according to claim 2, in combination with an internal cusp-shaped guide member carried by and facing upwardly from said base, and a follower depending from said upper member for following engagement with said guide member.

7. An articulator according to claim 2, in combination with an assembly surfacing device comprising a platform for supporting said assembly when being fed to surface a first face, and a feeding member upstanding from said platform generally normal thereto and shiftable therealong toward and away from a surfacing tool, whereby said feed member is engageable with said first face to feed said assembly and surface the opposite face generally parallel to said first face.

8. An articulator comprising a base adapted to rest on a supporting surface, a lower member in upwardly facing relation on said base for detachably carrying a lower dental model, upstanding pedestal means on said base, bearing means at an upper region of said pedestal means, journal means rotatably supported by said bearing means, an upper member extending from said journal means in downwardly facing relation over said lower member for detachably carrying an upper dental model and rotatable with said journal means for moving said dental models toward and away from each other, lower adjustment means mounting said lower member for selective vertical adjustment relative to said base, upper adjustment means mounting said upper member for selective adjustment transverse of said journal means toward and away from said lower member, said upper and lower members being adjustable to position the occlusal plane of said models, an internal cusp-shaped guide member carried by and facing upwardly from said base, and a follower depending from said upper member for following engagement with said guide member.

9. An articulator comprising a base adapted to rest on a supporting surface, a lower member in upwardly facing relation on said base for detachably carrying a lower dental model, upstanding pedestal means on said base, bearing means at an upper region of said pedestal means, journal means rotatably supported by said bearing means, an upper member extending from said journal means in downwardly facing relation over said lower member for detachably carrying an upper dental model and rotatable with said journal means for moving said dental models toward and away from each other, lower adjustment means mounting said lower member for selective vertical adjustment relative to said base, upper adjustment means mounting said upper member for selective adjustment transverse of said journal means toward and away from said lower member, said upper and lower members being adjustable to position the occlusal plane of said models, an assembly surfacing device comprising a platform for supporting said assembly when being fed to surface a first face, and a feeding member upstanding from said platform generally normal thereto and shiftable therealong toward and away from a surfacing tool, whereby said feed member is engageable with said first face to feed said assembly and surface the opposite face generally parallel to said first face.

* * * * *